(12) United States Patent
Girardot et al.

(10) Patent No.: US 6,506,339 B1
(45) Date of Patent: Jan. 14, 2003

(54) METHOD OF STERILIZATION

(75) Inventors: Jean-Marie Girardot, Dunwoody, GA (US); Marie-Nadia Girardot, Dunwoody, GA (US)

(73) Assignee: Biomedical Design, Inc., Marietta, GA (US)

( * ) Notice: Subject to any disclaimer, the term of this patent is extended or adjusted under 35 U.S.C. 154(b) by 0 days.

(21) Appl. No.: 09/325,511

(22) Filed: Jun. 3, 1999

Related U.S. Application Data

(63) Continuation-in-part of application No. 09/020,471, filed on Feb. 9, 1998, now Pat. No. 5,911,951.
(60) Provisional application No. 60/037,528, filed on Feb. 10, 1997.

(51) Int. Cl.$^7$ .............................. A61L 2/18; A01N 1/02
(52) U.S. Cl. ........................................ 422/28; 435/1.1
(58) Field of Search ........................... 422/28; 435/1.1; 8/94.11, 94.33

(56) References Cited

U.S. PATENT DOCUMENTS

| | | | |
|---|---|---|---|
| 4,378,224 A | 3/1983 | Nimni et al. | 8/94.11 |
| 4,383,832 A | 5/1983 | Fraefel et al. | 8/94.11 |
| 4,472,840 A * | 9/1984 | Jefferiesa | |
| 5,104,405 A | 4/1992 | Nimni | 623/2 |
| 5,447,536 A | 9/1995 | Girardot et al. | 8/94.11 |
| 5,697,972 A | 12/1997 | Kim et al. | 623/2 |
| 5,733,339 A | 3/1998 | Girardot et al. | 8/94.11 |

FOREIGN PATENT DOCUMENTS

| | | |
|---|---|---|
| EP | 0267434 | 10/1986 |
| WO | WO-9628196 A1 * | 9/1996 |

OTHER PUBLICATIONS

Rao, S. Bhaskara et al. "Sterilization of Chitosan: Implications," Journal of Biomaterials Applications, v.10 (2), 1995, pp. 136–143.*
Lee, et al., "Crosslinking of tissue–derived biomaterials in 1–ethyl–3–(3–dimethylaminopropyl)carbodiimide (EDC)", J. Mater. Sci.: Mater. Med., pp. 531–541, 1996.

* cited by examiner

*Primary Examiner*—Elizabeth McKane
(74) *Attorney, Agent, or Firm*—Fitch, Even, Tabin & Flannery

(57) ABSTRACT

Heart valves or other components for replacement of heart or other bodily organs and tissue prostheses or synthetic prosthetic materials are effectively sterilized by treatment with a carbodiimide coupling agent known to create amide linkages between amines and carboxylic acids. Such treatment has been shown to be bactericidal when carried out using an effective concentration of such a carbodiimide at a temperature of at least about 35° C. for a sufficient period of time, e.g. treatment for about 9 hours at a concentration of at least about 50 mM. The sterilization treatment preferably employs EDC as a water-soluble coupling agent. Such sterilization treatment of biological tissue that has previously been fixed by subjection to stabilizing cross-linking is preferably carried out in a buffered aqueous solution and leaves no residuals other than ones which are nontoxic and biocompatible; moreover, it does not affect the desirable characteristics of resistance to thermal denaturation and to digestion by proteolytic enzymes, which are a product of such prior fixing, and may actually increase the resistance of such fixed biological tissue to degeneration and calcification.

19 Claims, No Drawings

METHOD OF STERILIZATION

This application is a continuation-in-part of our pending application Ser. No. 09/020,471, filed Feb. 9, 1998, now U.S. Pat. No. 5,911,951, which application claims priority from U.S. Provisional Application Ser. No. 60/037,528, filed Feb. 10, 1997. The disclosures of both of these applications are incorporated herein by reference.

FIELD OF THE INVENTION

This invention relates to sterilization processes and more specifically to sterilization processes which are particularly suited for biological materials, such as organ replacements, and which methods exhibit efficacy against difficult-to-kill bacteria and bacterial spores.

BACKGROUND OF THE INVENTION

Sterilization techniques are widely used and important in industries such as food processing and health care. Saturated steam at temperatures above 110° C. has frequently been used to destroy microorganisms, such as microbial spores. Certain articles, particularly those used for health care, cannot withstand the temperatures and moisture of steam sterilization, and oftentimes such articles are also considered not to be suitable for sterilization by ionizing radiation. As a result, gaseous sterilants have been developed which function at relatively low temperatures and thus offer an attractive alternative. One of the most commonly used gaseous sterilants is ethylene oxide, which is used for medical product sterilization and for other sterilization processes. However, in certain instances, the presence of residual ethylene oxide, even in small quantities, is considered to be detrimental, and accordingly improved sterilization processes, particularly for sterilization of medical products, have continued to be sought.

SUMMARY OF THE INVENTION

It has now been found that sterilization of items, including biological tissue, replacement organs and synthetic prosthetic materials, including polymers and metals, can be effectively carried out by treatment with a coupling agent, e.g. a water-soluble carbodiimide, that is capable of creating amide linkages between amines and carboxylic acids; such treatment has been proven to be bactericidal. Sterilization treatment is carried out at a temperature above ambient, and although it may employ an optional coupling enhancer, such is not felt necessary. Treatment may be carried out using an organic solution of an appropriate coupling agent or using an aqueous buffered solution that may optionally contain isopropyl alcohol or the like, but the presence of such an alcohol is not necessary to achieve effective sterilization. The residuals from such treatment are nontoxic, biocompatible, and water-soluble; they can generally be easily be washed off the tissue before implantation in a human body. Surprisingly, biological tissue which has been effectively sterilized using a water-soluble carbodiimide may exhibit enhanced resistance to degeneration and/or calcification following its implantation within a living body.

DETAILED DESCRIPTION OF THE PREFERRED EMBODIMENTS

The term "coupling agent" is herein used to refer to a chemical reagent that facilitates the formation of amide bonds. Such bonds may be formed between reactive amines and reactive carboxyls on enzymes and proteins as well as between the reactive carboxyl or amine moieties located on and within bioprosthetic tissue. Those having skill in peptide synthesis and related arts will be familiar with some such reagents, e.g. water-soluble carbodiimides and succinimides; there are other known coupling agents that are soluble in organic solvents. When penetration of such coupling agents into the cells of microorganisms occurs, it results in sterilization, destroying bacteria, spores and possibly viruses and other infectious agents by internal cross-linking. When biological tissue is to be treated, the coupling agent chosen is preferably one that is water-soluble so the treatment can be effected in aqueous solution at a physiological pH. When other materials that are resistant to organic solvents are to be sterilized, e.g. synthetic polymeric materials, organic solutions of appropriately soluble coupling agents may be used. Any suitable carbodiimide can be used as the coupling agent; however, the preferred water-soluble coupling agent is 1-ethyl-3(3-dimethyl aminopropyl)carbodiimide hydrochloride (EDC). Other water-soluble carbodiimides include 1-Cyclohexyl-3(2-morpholinoethyl)carbodiimide, N,N'-Carbonyldiimidazole, Woodward's Reagent K, and mixtures of such carbodiimides. A list of such cross-linking coupling agents can be found in the book: Bioconjugate Techniques by Greg T. Hermanson published by Academic Press 1996, the relevant disclosure of which is incorporated herein by reference. When biological tissue is being treated, the water-soluble coupling agent EDC is preferably used. As indicated above, an optional enhancer, e.g. N-hydroxysulfosuccinimide (sulfo-NHS), might be included at a concentration between 0.5 mM and about 30 mM when EDC is used as the coupling agent; however, such is not considered necessary for effective sterilization.

The sterilization treatment is considered to be temperature-dependent, with a relatively low temperature of about 35–40° C. being preferred because of its lack of potential adverse effect upon the material being treated. The concentration of the coupling agent can be varied within a reasonable range, and treatment with higher concentrations of the coupling agent has been found to achieve sterilization within a shorter time of treatment. Although lower concentrations, e.g. 5–15 mM, may be effectively used, particularly when higher temperatures are employed, the coupling agent is preferably used in a concentration between about 25 millimolar (mM) and about 150 mM, more preferably between about 35 mM and about 100 mM, and most preferably at between about 50 mM and about 75 mM, in order to be certain of destroying all commonly encountered bacteria and spores within a reasonable duration of treatment.

Higher concentrations of coupling agent, so long as compatible with the material being sterilized, will generally reduce the duration of treatment needed. It has been found that effective sterilization is achieved when such treatment is carried out at a suitable temperature above ambient, e.g. at a temperature of at least about 35° C., for a minimum number of concentration-duration units, i.e. a multiple of coupling agent concentration and duration of exposure. By arbitrarily basing such units upon millimoles of the coupling agent and hours of sterilization treatment, it has been found that at a temperature of about 35–40° C., a minimum number of units equal to at least about 450 millimole hours should be employed. For example, effective sterilization may be achieved at a coupling agent concentration of about 50 mM for about 9–10 hours or alternatively at a concentration of about 25 mM for about 20–24 hours. At a concentration of about 120 mM, treatment at about 40° C. for about 6 hours should achieve sterilization. Although even higher concentrations, e.g. 150 mM, might be used, they are considered to be generally unnecessary and likely impractical from an economic standpoint. Moreover, by raising the temperature, e.g. to about 50–55° C., treatment for at least about 100–150 millimole hours should suffice, e.g. 3 hours with a concentration of 50 mM or 10 hours at 10 mM. Obviously, longer durations can be employed, and for purposes of safety, it may be desirable to employ such sterilization treatment for about 25–50% longer than the above-stated minimum that should achieve sterilization under normal conditions.

For purposes of this application, a particular sterilization treatment is deemed to be effective when it will effect a reduction of about $10^6$ (6 log) when about $10^6$ spores and/or microorganisms are inoculated in the test sample. This should assure that there will be no survivors in actual practice because biological tissue or other material that is being subjected to a sterilization treatment will not reasonably contain a level of microorganism contamination even approaching this magnitude. This treatment not only achieves sterilization without risk of damage to biological tissue that is to be implanted, but it may also make some contribution to stability of certain fixed biological tissue, e.g. the resistance of such biological tissue to degenerate and/or calcify within a living body may be enhanced.

Reaction conditions for the sterilization treatment may vary somewhat depending on the specific coupling agent employed. Sterilization treatment is frequently carried out using a water-soluble carbodiimide in an aqueous buffer solution selected from among buffers that are well known to those of ordinary skill in this art as being suitable buffers for use in the physiological pH range. Examples of suitable buffers include, but are not limited to, N-2-hydroxyethylpiperazine-N'-ethanesulfonic acid (HEPES), Tris(hydroxymethyl)aminomethane, 3-(N-morpholino) propanesulfonic acid (MOPS), N-Tris(hydroxymethyl) methyl-2-aminoethane sulfonic acid, N-Tris (hydroxymethyl)methylglycine, and the like.

The pH and concentration of buffer in an aqueous solution also may vary depending upon the coupling agent employed. The buffer concentration and pH are chosen to provide an effective sterilization environment while being the least harmful to bioprosthetic or other material being treated. For example, with EDC as the coupling agent for sterilizing biological tissue, the pH of the aqueous solution employed is about 6.0 to about 7.0 and the temperature is usually maintained between about 35° C. and 40° C. As mentioned above, higher temperatures may be used so long as they are compatible with the materials being sterilized; however, temperatures above about 55° C. are not generally used, for example, with medical devices made of bioprosthetic tissue. Preferably, sterilization is carried out at about 40° C. or above. For sterilizing polymeric or metallic materials, temperatures slightly higher than 55° C., i.e. about 75° C., may be used so long as they are not harmful to the material being sterilized, and use of such higher temperatures may shorten the necessary duration of treatment. All sterilization treatment solutions are preferably filtered through 0.45 $\mu$m or smaller filters before use to eliminate possible contamination. The optional inclusion in such solution of a small volume % of a $C_2$ to $C_4$ alkanol or an equivalent alcohol may permit sterilization at a lower temperature and/or with a lower percentage of coupling agent; however, isopropanol or the like may have an adverse effect upon certain tissue, in which case such sterilization should be carried out in the absence of an alkanol.

This sterilization treatment method is considered useful for a wide variety of prosthetic and bioprosthetic materials; however, it is considered to be particularly useful for sterilizing replacement organ components, such as heart valves, which have been made from animal tissue that has been suitably fixed. By suitably fixed is meant having been subjected to cross-linking ("fixing"), as by glutaraldehyde treatment or by a comparable process such as described in U.S. Pat. Nos. 5,447,536 and 5,733,339 so as to raise the shrinkage temperature thereof. Other fixation techniques, e.g. polyepoxide crosslinking or photo-oxidation may also be used. In some instances, it may be important that, if biological tissue is being fixed, it has been at least minimally fixed; otherwise, the chemical action of the coupling agent might be diverted.

It may be desirable to first rinse the material with cold saline prior to sterilization as a preparation therefor, because sterilization is usually a final step before use or packaging. The material being sterilized is usually maintained in contact with the sterilization solution for about 6 to 48 hours, and such treatment has been shown to effectively inactivate even hard-to-kill bacteria and spores, thus proving the process to be potently bactericidal. It is common in the industry to "quarantine" such sterilized products for 1 to 2 weeks, during which time the bioindicator results of sterilization will be received. The product is then considered ready for packaging or temporary storage. Thereafter, it is ready for immediate use following one or more sterile rinses to remove any remaining unreacted reagents and by-products. This sterilization treatment has not been shown to adversely affect bioprosthetic tissue, as by possibly lowering the shrinkage temperature of such sterilized material or by lowering its resistance to proteolytic degradation by collagenase or by proteases; on the contrary, in some instances, it may increase shrinkage temperature and/or surprisingly increase resistance of biological tissue to calcification.

The present invention is further described by the examples that follow. These examples are not to be construed as limiting in any way either the spirit or the scope of the present invention.

Devices to be implanted in the human body are required to be sterilized in a manner to effectively destroy all microorganisms. Due to the unique applications of liquid chemicals for use in sterilization processes, it is necessary to be vigilant in detecting, screening and testing microorganisms which could pose significant resistance to the sterilization process. Examples of reference microorganisms which have previously demonstrated high resistance to liquid chemical sterilants are: the spores of *Bacillus subtilis, Clostridium sporogenes, Bacillus pumilus, Chaetonium globosom* and *Microascus cinereus* and representative vegetative cells, such as *Mycobacterium chelonae, Methylbactrium extorquens,* and *Trichosporon aquatile.* Of the foregoing, the most resistant may be the spores of *Bacillus subtilis.* The coupling agent used in the following examples is 1-ethyl-3 (3-dimethyl aminopropyl)carbodiimide hydrochloride (EDC), and when used, the optional enhancer is either N-hydroxysulfosuccinimide (sulfo-NHS) or hydroxysuccinimide (NHS), which are all commercially available. Peptone water is prepared by dissolving 1 g of Bacto Peptone in 1 liter of de-ionized water. The solution is then filtered into sterile bottles using sterile 0.2 micron filters. All agents are solubilized in 10 mM HEPES buffer containing 0.85% of sodium chloride, pH 6.5 (HEPES buffer). Concentrations are expressed as mM (number of millimoles of chemical for each liter of solution), or as % (grams per 100 ml of solution). Temperatures are in ° C. (degrees Celsius), with room temperature being about 20–25°.

Porcine aortic roots are fixed by cross-linking according to the method described in U.S. Pat. No. 5,447,536. After fixation, the valves are stored in 10 mM HEPES, 0.85%

NaCl, 20% isopropyl alcohol, pH 7.4, at 4° C. The sterility tests described in the following examples are in most cases conducted in the presence of bioprosthetic heart valve tissue; when such tissue is not present, the solutions are simply filtered through a 0.45 micron filter attached to a funnel (filter funnel). The filters are then rinsed with peptone water to eliminate residual chemicals on the membrane that may prevent growth of the organisms tested. Such membrane filters are then incubated on TSA plates at about 32° to 33° C., e.g. 32.5° C. When an aortic valve is inoculated with microorganisms for test purposes and then submitted to sterilization, the solution is filtered as described above. The aortic valve tissue is then washed for 20 minutes in a reciprocating shaker in the presence of peptone water containing Tween 80 in order to extract all indigenous spores or microorganisms from the tissue. This solution is filtered and then incubated as described above. All microbiological testing is performed in a biological laminar flow hood to prevent contamination. The shrinkage temperature and the proteolytic (collagenase and protease) degradation tests are conducted as previously described in the '536 patent. Resistance to calcification is assessed by subdermal implantation of sterilized leaflets and aortic wall coupons in young rats, as also described in the '536 U.S. patent.

EXAMPLE 1

Mycobacterium Chelonae ATCC 35752 (~$10^5$) was inoculated in sterile cups. A 10 mM HEPES, 0.85% NaCl, pH 6.5 solution containing 10 mM EDC and 1 mM Sulfo-NHS in the presence or absence of 20% isopropyl alcohol was maintained in contact with the bacteria in the cups for various periods of time (treatment duration). The cups were maintained at room temperature, and the solutions were then filtered. The filters were then incubated at about 32–33° C. for up to 6 weeks (incubation duration) using either Trypticase Soy Agar (TSA) plates or Trypticase Soy Broth (TSB). All inoculations were done in duplicate.

| Treatment | RESULTS | | | | |
|---|---|---|---|---|---|
| | Incubation Duration | | | | |
| Duration | 1 Day | 1 Week | 3 Week | 4 Week | 6 Week |
| NO ISOPROPYL ALCOHOL | | | | | |
| 0 hour | +,+ | +,+ | +,+ | +,+ | +,+ |
| 12 hours | +,+ | +,+ | +,+ | +,+ | +,+ |
| 24 hours | -,- | +,+ | +,+ | +,+ | +,+ |
| 48 hours | -,- | -,- | -,- | -,- | -,+ |
| 72 hours | -,- | -,- | -,- | -,- | -,+ |
| | TSA,TSB | TSA,TSB | TSA,TSB | TSA,TSB | TSA,TSB |
| (+) Indicates growth while (-) indicates no growth. | | | | | |
| 20% ISOPROPYL ALCOHOL | | | | | |
| 0 hour | -,- | -,- | +,+ | +,+ | +,+ |
| 12 hours | -,- | -,- | -,- | -,- | -,- |
| 24 hours | -,- | -,- | -,- | -,- | -,- |
| 48 hours | -,- | -,- | -,- | -,- | -,- |
| 72 hours | -,- | -,- | -,- | -,- | -,- |
| | TSA,TSB | TSA,TSB | TSA,TSB | TSA,TSB | TSA,TSB |

(+) Indicates growth while (-) indicates no growth or complete kill.

The results indicate that, in the presence of 20% isopropyl alcohol, room temperature treatment with EDC plus Sulfo-NHS kills all Mycobacterium chelonae within 12 hours of sterilization treatment.

EXAMPLE 2

A sterilization process similar to Example 1 is carried out using Bacillus Subtilis spores (~$10^6$) inoculated in sterile cups some of which contain cross-linked heart valves that had been fixed by a process according to U.S. Pat. No. 5,447,536. A 10 mM HEPES, 0.85% NaCl, pH 6.5 solution containing 20 mM EDC and 1 mM Sulfo-NHS in the presence of 20% isopropyl alcohol was added for various periods of time (treatment duration). The cups and the heart valves were maintained at 40° C. for the term of the treatment. The solutions were then filtered and the filters incubated for up to 7 days (incubation duration) at about 32–33° C. using Trypticase Soy Agar (TSA) plates. All inoculations were done in duplicate.

| RESULTS | | |
|---|---|---|
| | Incubation Duration | |
| Treatment Duration | 1 Day | 7 Days |
| WITHOUT VALVES | | |
| 24 hours | - | - |
| 48 hours | - | - |
| 72 hours | - | - |
| WITH VALVES | | |
| 48 hours | - | - |
| 72 hours | - | - |

(+) indicates growth, while (-) indicates no growth or complete kill.

The results demonstrate that the spores of Bacillus subtilis are inactivated with this method of sterilization in the absence or presence of porcine aortic valve tissue.

EXAMPLE 3

In the experiments described above, a coupling enhancer (Sulfo-NHS) was added to EDC during the sterilization process. The following experiment was designed to test the efficacy of EDC in the presence or absence of an enhancer. A sterilization test process was carried out employing about 5.7 to 6.6×$10^5$ Bacillus subtilis ATCC 9372 spores, inoculating them in sterile cups for 10 minutes. A solution of 10 mM HEPES, 0.85% NaCl, 20% isopropyl alcohol, pH 6.5 was then added to each of the cups, which solution contained 20 mM EDC and either 1 mM Sulfo-NHS or 1 mM NHS or no enhancer. Incubation was carried out for 72 hours (treatment duration) with the cups at about 40° C., and the solutions from the cups were then filtered. The filters were rinsed with a 0.1% peptone water solution to eliminate any residual EDC and/or enhancer and were then incubated on Trypticase Soy Agar (TSA) plates. All inoculations were done in duplicate, and the results are set forth in Table A.

TABLE A

| | | NUMBER OF COLONY FORMING UNITS (SURVIVORS) | | |
|---|---|---|---|---|
| | | ENHANCER | | |
| CONDITIONS | SAMPLES | sulfo-NHS | NHS | NONE |
| CONTROLS | | | | |
| negative | 1 | 0 | 0 | 0 |
| | 2 | 0 | 0 | 0 |
| positive | 1 | 5.7 × $10^5$ | 6.1 × $10^5$ | 6.6 × $10^5$ |
| | 2 | 5.7 × $10^5$ | 6.5 × $10^5$ | −6.0 × $10^5$ |
| TESTS | 1 | 0 | 0 | 0 |
| | 2 | 0 | 0 | 0 |

The results demonstrate that EDC and isopropanol, either in the presence or absence of an enhancer such as sulfo-NHS or NHS, is a potent bactericide against the spores of Bacillus subtilis.

EXAMPLE 4

The following experiment was designed to test the effect of EDC concentration, of temperature and of duration of incubation on the inactivation of spores of Bacillus subtilis. The EDC concentrations tested were 5, 12.5 and 20 mM; the temperatures were 25, 32.5 and 40° C. for 4, 24 and 44 hours of incubation. The tests were carried out under the conditions as hereinafter set forth in Table B using aqueous solutions that were 10 mM HEPES at a pH of 6.5 and contained 0.85% NaCl and 20% IPA so as to be comparable to Examples 2 and 3. Spores of Bacillus subtilis (about $2.5 \times 10^5$ per sample) were inoculated on tissue that had been cross-linked using the fixation method described in the '536 patent. The spores were allowed to contact the tissue for 10 minutes, after which time 50 ml of a solution of EDC at one of the concentrations indicated above was added to each cup containing the tissue plus the spores, and incubation was carried out at the respective temperatures and for the respective lengths of time. After such incubation for either 4, 24 or 44 hours, the solutions were filtered to recover the spores, and these were incubated on TSA plates for 2 weeks at 32 to 33° C. The tissue samples were washed with a solution containing a surfactant to fully extract the spores from the tissue, and the resulting solutions were filtered. After washing with 0.1% peptone water, the filters were incubated on TSA plates for 2 weeks at 32 to 33° C. in order to determine the number of survivors on or in the tissue. The colonies were enumerated for both the EDC solutions and the tissue wash solutions, and the results (numbers of colony forming units) were added. The positive and negative controls were shown to be valid for the test. The experimental results are presented in Table B.

TABLE B

| CON-DITION | EDC (mM) | TEMP. ° C. | TIME (hrs) | SURVIVORS # CFUs | LOG REDUCTION |
|---|---|---|---|---|---|
| 1 | 5 | 25 | 4 | 135000 | .27 |
| 2 | 5 | 25 | 44 | 1300 | 2.3 |
| 3 | 5 | 32.5 | 24 | 208 | 3.0 |
| 4 | 5 | 40 | 4 | 1100 | 2.4 |
| 5 | 5 | 40 | 44 | 21 | 4.1 |
| 6 | 12.5 | 25 | 24 | 225 | 3.0 |
| 7 | 12.5 | 32.5 | 4 | 5900 | 1.6 |
| 8 | 12.5 | 32.5 | 24 | 57 | 3.6 |
| 9 | 12.5 | 32.5 | 24 | 34 | 3.9 |
| 10 | 12.5 | 32.5 | 24 | 94 | 3.4 |
| 11 | 12.5 | 32.5 | 24 | 44 | 3.7 |
| 12 | 12.5 | 32.5 | 44 | 33 | 3.9 |
| 13 | 12.5 | 40 | 24 | 27 | 4.0 |
| 14 | 20 | 25 | 4 | 31400 | 0.9 |
| 15 | 20 | 25 | 44 | 16 | 4.2 |
| 16 | 20 | 32.5 | 24 | 24 | 4.0 |
| 17 | 20 | 40 | 4 | 5 | 4.7 |
| 18 | 20 | 40 | 44 | 0 | 5.4 |

The results demonstrate that the bactericidal activity of EDC is dependent on the concentration of EDC, the temperature of incubation and the duration of incubation. In addition, it can be seen that EDC at 20 mM concentration kills all the spores on cross-linked tissue at some time between 4 and 44 hours at 40° C. because a logarithmic reduction of about 4.7 was obtained after 4 hours of incubation at 40° C., and because no survivors were present after 44 hours of incubation. Moreover, the fact that s logarithmetic reduction of about 4 was achieved at 40° C. after 44 hours of incubation, in the presence of only 5 mM EDC, indicates that EDC in the presence of 20% IPA is a potent bactericidal agent.

EXAMPLE 4A

The following experiment was carried out to assess the effectiveness of a coupling agent, such as EDC, in the absence of isopropyl alcohol or an equivalent alkanol. Bacillus subtilis (niger) spores at levels of $1.5 \times 10^6$ were inoculated in sterile cups for approximately 10 minutes. Solutions (50 ml) of 25, 37.5 and 50 mM EDC in 10 mM TRIS, 0.85% NaCl, pH 6.5, which contain no isopropyl alcohol, were prewarmed to 40° C. and then rapidly added to the cups. The cups were incubated at 40° C. for 0.5, 1, 6, 24 and 48 hours; then, the solutions were diluted and filtered in order to collect microorganisms. Next, the filters were rinsed with a 0.1% peptone water solution to eliminate any residual EDC and then incubated on TSA plates for up to 14 days. The plates were examined every day for growth, with the colony forming units (CFUs) being counted, and resulting D values were calculated. Such D values represent the duration (in minutes) of incubation to decrease the level of spores by one log, i.e. eliminating 90% of the spores population.

The results for D values for treatment with 25, 37.5 and 50 mM EDC were respectively found to be 203, 106 and 86 minutes. From this data, the incubation duration necessary to achieve 6 log reduction (or effective inactivation of $1 \times 10^6$ spores) is calculated as 24 hours, 11 hours and 9 hours, respectively. The results show that sterilization efficacy increases as a function of EDC concentration and also that complete inactivation of the spores of Bacillus subtilis can be achieved in the absence of isopropyl alcohol at 40° C. given longer duration of incubation and higher EDC concentrations.

For safety reasons, it may be desirable to employ a duration of incubation for sterilization under such conditions that is about 10–35% higher than the hours given above to insure complete inactivation of all microorganisms present.

EXAMPLE 4B

An experiment similar to that of Example 2 is carried out using EDC as a coupling agent in the absence of isopropyl alcohol and sulfo-NHS. Bacillus subtilis (niger) spores at levels of about $10^6$ are inoculated in sterile cups, some of which contain cross-linked porcine aortic valve tissue, for approximately 10 minutes. Solutions (50 ml) of 25, 50 and 70 mM EDC in 10 mM TRIS, 0.85% NaCl, pH 6.5, are prewarmed to 40° C., respectively added to the cups, and incubated at 40° C. for 1 to 3 days. The solutions are then diluted and filtered in order to collect microorganisms. The valve tissue is washed for 20 minutes in a reciprocating shaker in the presence of peptone water containing polyethylenesorbitan monooleate (Tween 80) in order to extract all spores of microorganisms from the tissue; the peptone water solution is added to the corresponding filter. Next, the filters are rinsed with a 0.1% peptone water solution to eliminate any residual EDC and incubated on TSA plates for 14 days. The plates are examined every day for growth, counting the colony forming units (CFUs). The results show that effective sterilization occurs within 24 hours under these conditions whether in the presence or the absence of porcine tissue, thus demonstrating that treatment with 25, 50 or 70 mM EDC at 40° C. effectively inactivates $1 \times 10^6$ spores after 24 hours in the absence of isopropyl alcohol.

EXAMPLE 4C

An experiment similar to that of Example 4A is carried out using slightly higher concentrations of EDC and including porcine aortic root tissue. Bacillus subtilis (niger) spores at levels of $1.5 \times 10^6$ are inoculated for approximately 10 minutes in sterile cups each containing root tissue. Solutions (50 ml) of 50, 75 and 100 mM EDC in 10 mM TRIS, 0.85%

NaCl, pH 6.5 are prewarmed to 40° C. and then rapidly added to the tissues in the cups. The cups containing the tissue are incubated at 40° C. for 6, 9, 12, 24 and 48 hours; then, the solutions are diluted and filtered in order to collect microorganisms. The valve tissue is washed for 20 minutes in a reciprocating shaker in the presence of peptone water containing Tween 80 in order to extract all spores of microorganisms from the tissue. The solutions from the shakers are filtered through the respective filters to which the original solutions were applied. The filters are rinsed with a 0.1% peptone water solution and incubated on TSA plates for up to 14 days. The plates are examined daily for growth. The results demonstrate that treatment with 75 and 100 mM EDC at 40° C. effectively inactivates these spores after 6 hours, while only partial kill is achieved by treatment with 50 mM EDC. However, after 9 hours, effective sterilization resulting in complete inactivation of the spores of *Bacillus subtilis* is achieved by incubation with all 3 EDC concentrations at 40° C.

EXAMPLE 4D

An experiment similar to that of Example 4A was carried out using a higher temperature of 55°. *Bacillus subtilis* (*niger*) spores at levels of $1.32 \times 10^6$ ($Log_{10}=6.12$) were inoculated for approximately 10 minutes in sterile cups. Solutions (50 ml) of 5 and 50 mM EDC in 10 mM TRIS, 0.85% NaCl, pH 6.5 were prewarmed to 55° C. and then rapidly added to the cups. The cups were incubated at 55° C. for 1 and 10 hours; the solutions were then diluted and filtered in order to collect microorganisms. The filters were rinsed with a 0.1% peptone water solution and incubated on TSA plates for up to 14 days. The plates are examined daily for growth. The results demonstrate that treatment with 50 mM EDC at 55° C. effectively inactivated these spores after 10 hours, while a log reduction of 3.04 was achieved by treatment with 50 mM EDC at 55° C. for only one hour. This can be extrapolated to achieving complete kill in 2–3 hours. Treatment with 5 mM EDC for 1 hour resulted in a log reduction in the spores of *Bacillus subtilis* of 0.512; whereas the 10-hour treatment at 55° C. resulted in a log reduction of 4.46. Although this cannot be extrapolated to complete kill over a greater length of time because of the low level of EDC remaining after 10 hours, it is expected that sterilization treatment using a concentration at least about 15 mM EDC at 55° C. for 10 hours would result in complete kill.

EXAMPLE 5

An experiment was also designed to test the bactericidal activity of the EDC treatment using two sequential inoculations of at least $1 \times 10^6$ spores of *Bacillus subtilis* per sample. In the first step, $1.43 \times 10^6$ spores ($Log_{10}=6.2$) were inoculated in triplicate for 10 minutes onto 45 porcine valves which had been cross-linked using a method as described in the above-mentioned patent and patent application. Solutions of 25 mM EDC in 10 mM HEPES, 0.85% NaCl, 20% isopropyl alcohol, at pH 6.5 were poured into the cups containing the valve samples. After 2, 4, 6, and 8 hours of incubation at 40° C., the total surviving spores from 12 samples (solution plus tissue) were counted. After 8 hours of incubation, an additional $1.2 \times 10^6$ ($Log_{10}=6.1$) spores were added to the remaining 33 samples. Summarizing, these remaining 33 samples were thus inoculated at t=0 with $1.43 \times 10^6$ spores and at t=8 with $1.2 \times 10^6$ spores. After various durations of incubation (see Table C for details), the surviving spores in solution and on the valve tissue were removed by filtering and incubated on TSA plates as described above. The positive and negative controls were determined to be valid for the test.

The results are presented in Table C which follows. The results demonstrate that a 6.2 log reduction (no survivors) of *Bacillus subtilis* spores is achieved within 6 hours of incubation with EDC in the presence of isopropanol and that another 6.1 log reduction is achieved within 6 hours after rechallenge. Complete sterilization of the tissue valve samples and the solution was achieved in this manner.

TABLE C

| Incubation | Mean of Three Samples | | |
|---|---|---|---|
| Duration Hours @ 40° C. | Total Survivors # CFUs | Total Survivors Log 10 | LOG Reduction |
| 0 | $1.43 \times 10^6$ | 6.2 | 0 |
| 2 | 58 | 1.7 | 4.5 |
| 4 | 4 | 0.5 | 5.6 |
| 6 | 0 | 0 | 6.2 |
| 8 | 0 | 0 | 6.2 |
| 8 Rechallenge | $1.2 \times 10^6$ | 6.1 | n/a |
| 11 | 300 | 2.5 | 3.7 |
| 14 | 0 | 0 | 6.1 |
| 20 | 0 | 0 | 6.1 |
| 24 | 0 | 0 | 6.1 |
| 28 to 56 | 0 | 0 | 6.1 |

EXAMPLE 6

The foregoing experiments have generally shown that the sterilization effect of EDC plus a lower alkanol could be equally demonstrated by testing biological tissue which had inoculated with bacteria or by simply testing similar amounts of bacteria which have been inoculated into sterile cups. In view of the foregoing verification, it was decided to test the effectiveness of the sterilization process against other bacteria using sterile cups. Added to each of the cups is 20 ml of 10 mM HEPES, 0.85%, Nacl, 20% isopropanol, pH 6.5, containing 25 mM EDC without any coupling enhancer, before the cups are placed in a incubator at about 38° C. When the solution temperature reached about 38° C., approximately $10^5$–$10^6$ organisms were inoculated into the solution. The tests were carried out in triplicate. The following four isolated were tested in the form of sporous suspensions: *Clostridium sporogenes* ATCC 3584, *Bacillus pumilus* ATCC 27142, *Chaetonium globosom* ATCC 6205, and *Microacus cinereus* ATCC 16594. The following three isolates were tested as vegetative cells: *Mycobacterium chelonae* ATCC 35752, *Methylbacterium extorquens* ATCC 43645 and *Trichosporon aquatile* ATCC 22310. The inoculated systems were allowed to incubate for 1 hour, for 5 hours or for 24 hours, and the solutions were then filtered through a 0.45 micron filter. After rinsing, the filter was placed on a TSA plate as described in Example 1. Negative and positive controls indicate that the tests were valid. The results are set forth in Table D which follows wherein the number of CFUs in the inoculum is expressed as its log to the base 10, e.g. $3.4 \times 10^5 = 5.5$:

TABLE D

| ORGANISM | INOCULUM Log 10 | Log REDUCTION 1 Hour | 5 Hours | 24 Hours |
|---|---|---|---|---|
| SPORES | | | | |
| Clostridium sporogenes | 4.6 | 2.12 | 3.02 | — |
|  | 3.65 | — | — | 3.65 |
| Bacillus pumilus | 5.45 | 3.68 | 4.41 | — |
|  | 5.22 | — | — | 5.22 |
| Chaetonium globosum | ~4.7 | — | (72 hrs.)* | (96 hrs.)* |
| VEGETATIVE CELLS | | | | |
| Methylobacterium extorquens | 6.94 | 6.94 | 6.94 | — |
| Trichosporon aquatile | 4.3 | 4.3 | 4.3 | — |
| Mycobacterium chelonae | 5.15 | 5.15 | — | — |

*no growth was observed after stated hours of incubation of plates.

The results indicate that, after one hour of incubation, all vegetative cells had been effectively inactivated. The more resistant spores of certain bacteria were inactivated in a time-dependent manner within 24 hours of incubation with sterilant. The tests show that, against forms of representative bacteria, EDC in the presence of isopropanol is a very good sterilant showing time-dependent inactivation of spores at about 38° C.

EXAMPLE 7

To determine any potentially adverse effect this sterilization may have on shrinkage temperature of the tissue, porcine aortic valves, which had been cross-linked using the method described above in the pending '076 patent application by treatment with EDC in the presence of either sulfo-NHS or NHS as a coupling enhancer, were sterilized using 25 mM EDC in 10 mM HEPES, 0.85% NaCl, 20% isopropyl alcohol, pH 6.5, at 40° C. for 24 hours. This duration of incubation has been shown in Table C to twice achieve a logarithmetic reduction of spores of Bacillus subtilis of about 6 in the sequential testing. The leaflets were dissected and the thermal denaturation temperature was determined for each as described in the '536 patent. The results are presented in Table E and demonstrate that this sterilization method has no adverse effect on the shrinkage temperature of the tissue regardless of which fixation process had been used.

TABLE E

| | DENATURATION TEMPERATURE (° C.) | | | |
|---|---|---|---|---|
| SAMPLES | NHS | NHS STERILIZED | sulfo-NHS | sulfo-NHS STERILIZED |
| LEAFLETS | 85.6 ± 0.2 | 85.0 ± 0.2 | 87.5 ± 0.3 | 87.0 ± 0.2 |

It can be seen from Table E that the shrinkage temperature does not change after sterilization.

To determine any effect this sterilization may have on susceptibility of the tissue to proteolytic degradation, porcine aortic valves similarly cross-linked using the method described in the pending patent application in the presence of either sulfo-NHS or NHS as coupling enhancer were sterilized, using 25 mM EDC in 10 M HEPES, 0.85% NaCl, 20% isopropyl alcohol, pH 6.5, at 40° C. for 24 hours. Aortic valve leaflets and aortic wall coupons were dissected, and they were then submitted to standard collagenase and protease degradation testing. Such testing is described in detail in the previously mentioned patent and patent application. The results of collagenase digestion testing are expressed as nanomoles of amine released per mg of dry tissue and are presented in Table F.

TABLE F

| | AMINES RELEASED (nmol/mg dry tissue) | | | |
|---|---|---|---|---|
| SAMPLES | NHS | NHS STERILIZED | sulfo-NHS | sulfo-NHS STERILIZED |
| LEAFLETS | 12.0 ± 0.3 | 12.4 ± 1.2 | 14.5 ± 1.5 | 14.9 ± 1.3 |
| AORTIC WALL | 12.3 ± 0.6 | 10.9 ± 0.5 | 13.1 ± 0.8 | 10.0 ± 0.5 |

The results are presented as means±SEM of six samples. There is no significant difference for the leaflets before and after sterilization, $p=0.718$ and $p=0.994$ for NHS and sulfo-NHS respectively. For the aortic wall coupons, there is a significant difference which indicates that they exhibit greater resistance to collagenase after sterilization, i.e., $p=0.046$ and $p=0.0099$ for NHS and sulfo-NHS, respectively. Thus, not only is the resistance to collagenase digestion not adversely affected by this EDC sterilization, in some instances, it may be improved. For comparison, previous experiments conducted under similar conditions showed that the level of amines released from fresh tissue were approximately 2150 and 430 nanomoles/mg of tissue for leaflets and aortic wall coupons, respectively.

The results of protease digestion testing are presented in Table G; results for glutaraldehyde-fixed tissue are also shown for comparison purposes. They indicate that there is no significant difference as a result of this sterilization of tissue cross-linked according to the method described in the '076 patent application when either NHS or sulfo-NHS is used as a coupling enhancer; the results obtained following the use of EDC for sterilization for either leaflets on aortic wall coupons show no adverse effect and a resistance equal to that of glutaraldehyde fixation.

TABLE G

| SAMPLES | GLULTARALDE-HYDE-FIXED | NHS | NHS STERILIZED | sulfo-NHS | sulfo-NHS STERILIZED |
|---|---|---|---|---|---|
| LEAFLETS | 31.6 ± 5.7 | 28.1 ± 1.7 | 32.3 ± 1.3 | 29.5 ± 2.6 | 31.9 ± 2.2 |
| AORTIC WALL | 74.5 ± 1.2 | 73.8 ± 1.0 | 75.1 ± 0.9 | 75.1 ± 0.9 | 75.6 ± 2.2 |

To determine the effect this sterilization may have on resistance to calcification, samples of (a) glutaraldehyde-fixed porcine aortic valve leaflets and of (b) porcine aortic valve leaflets cross-linked according to the method of the '076 patent application, which were sterilized using EDC in the presence of isopropanol as described above for the shrinkage temperature experiment, were implanted subdermally in young rats for four weeks. The samples were then retrieved, and quantitative calcium analysis was conducted using Atomic Absorption Spectrophotometry. The results are presented as means±SEM of six samples per condition in the following Table H.

TABLE H

| SAMPLES | Glutaraldehyde-fixed (n = 4) | NHS before ster. (n = 6) | NHS after ster. (n = 6) | sulfo-NHS before ster. (n = 6) | sulfo-NHS after ster. (n = 6) |
|---|---|---|---|---|---|
| LEAFLETS | 195 ± 8.9 | 23.7 ± 11.4 | 2.9 ± 1.4 | 25.2 ± 10.9 | 0.9 ± 0.1 |
| AORTIC WALL | 66.8 ± 4.5 | 53.2 ± 4.7 | 35.4 ± 6.1 | 54.2 ± 1.5 | 43.6 ± 3.5 |

The results demonstrate that the sterilization method using EDC at 25 mM in the presence of 20% isopropyl alcohol at 40° C. has no adverse effect on the resistance of the porcine aortic valve tissue to calcification. Moreover, it surprisingly shows that the sterilized samples are more resistant to calcification than the samples that were not sterilized. In addition, all the samples cross-linked according to the above-identified patent application are significantly less calcified than samples that had been cross-linked according to the standard glutaraldehyde method.

The results indicate that a solution of EDC in the presence of 20% isopropyl alcohol at about 40° C., with or without NHS or sulfo-NHS, is a powerful bactericide against spores of *Bacillus Subtilis* and other bacteria. Vegetative cells of *Mycobacterium Chelonae* were effectively inactivated at room temperature by EDC+Sulfo-NHS in the presence of 20% isopropyl alcohol, and subsequent tests with a variety of other vegetative cells showed that 25 mM EDC in 20% isopropanol is an effective sterilant for biological tissue. It is believed that treatment with a coupling agent in the presence of isopropyl alcohol or an equivalent alkanol and at slightly elevated temperature, and optionally with a coupling enhancer, has a potent bactericidal effect and is excellently suited for treatment of tissue valves, and is also considered suitable for sterilizing polymers, metals and the like. In addition, not only are the denaturation temperature and the resistance to proteolytic degradation of tissue valves not adversely affected by such sterilization treatment of 12 hours or more, but surprisingly, samples which have been sterilized using this process appear to be significantly more resistant to calcification, the leading cause of tissue valve failure. Compared to tissue fixed by the standard glutaraldehyde method, sterilization of heart valve tissue using the present method results in an unexpected increase in calcification resistance which should be quite important commercially.

Although the invention has been described with regard to certain preferred embodiments which constitute the best mode presently known by the inventors for carrying out the invention, it should be understood that changes and modifications that would be obvious to one having the ordinary skill in this art may be made without departing from the scope of the invention which is set forth in the claims appended hereto. For example, although the invention has been described with regard to the sterilization of porcine aortic valves and the like, it may also be used to sterilize polymeric or metal heart valve components or other components for implantation within the human body. The disclosures of all U.S. patents to which reference was made hereinbefore are expressly incorporated by reference.

Particular features of the invention are set forth in the claims which follow.

What is claimed is:

1. A process for sterilization of material, which process comprises treating such material with a solution containing an effective amount of a coupling agent capable of creating amide bonds and maintaining such treatment for a time and at a temperature which is sufficient to kill microorganisms carried by such material, which treating is effective to cause at least a log 6 reduction in spores and bacteria that may have a resistance to chemical sterilants as great as that of *Bacillus subtilis*.

2. The process for sterilization according to claim 1 wherein said treatment is carried out at a temperature of at least about 35° C.

3. The process for sterilization according to claim 1 wherein said treatment is carried out at a temperature of between about 40° and about 55° C.

4. The process for sterilization according to claim 3 wherein said coupling agent is present in said solution at a concentration of at least about 15 mM.

5. The process for sterilization according to claim 1 wherein said coupling agent is a water-soluble carbodiimide and is present in an aqueous solution at a concentration of at least about 50 mM.

6. The process for sterilization according to claim 5 wherein said aqueous solution contains a buffer and has a pH of about 6 to 7.

7. The process for sterilization according to claim 5 wherein said treatment is carried out for at least about 9 hours at a temperature of at least about 40° C.

8. The process for sterilization according to claim 1 wherein said solution is an aqueous solution and said coupling agent is EDC.

9. The process for sterilization according to claim 8 wherein EDC is present at a concentration of at least about 25 millimolar and said treatment is carried out for at least about 24 hours at a temperature of at least about 40° C.

10. The process for sterilization according to claim 1 wherein said treatment is carried out at a temperature of about 35–40° C. for a period of concentration-time units of at least about 450 millimole hours.

11. A process for sterilization of biological tissue that has been previously subjected to cross-linking to improve stability, which process comprises treating such biological tissue at a temperature of at least about 35° C. with an aqueous solution containing a concentration of at least about 25 mM of a water-soluble carbodiimide coupling agent that is capable of creating amide bonds for a period of concentration-time units sufficient to effectively kill any bacteria and spores carried by such biological tissue.

12. The process for sterilization according to claim 11 wherein a period of at least about 450 millimole-hours is used.

13. The process for sterilization according to claim 12 wherein said solution contains a concentration of at least about 50 mM EDC and wherein said treatment is carried out at between 40° C. and about 55° C.

14. The process for sterilization according to claim 11 wherein a period of at least about 100 millimole-hours is used and wherein the temperature of said treatment is maintained at about at least 55° C.

15. The process for sterilization according to claim 11 wherein said solution contains EDC as said water-soluble coupling agent at a concentration of at least about 35 mM.

16. A process for sterilization of biological material, which process comprises treating such material with an aqueous solution containing a concentration of at least about 50 mM of a water-soluble carbodiimide coupling agent capable of creating amide bonds, at a temperature of at least about 40° C., and maintaining such treatment for a time which is sufficient for said coupling agent to effectively kill spores and bacteria that may be carried by such material.

17. The process for sterilization according to claim 16 wherein said treatment is carried out at a temperature of between about 40° and about 55° C.

18. The process for sterilization according to claim 16 wherein said aqueous solution is buffered to a pH of about 6 to 7.

19. The process for sterilization according to claim 16 wherein said coupling agent is EDC.

* * * * *